United States Patent
Anderberg et al.

(10) Patent No.: US 10,794,917 B2
(45) Date of Patent: Oct. 6, 2020

(54) METHODS AND COMPOSITIONS FOR DIAGNOSIS AND PROGNOSIS OF APPENDICITIS AND DIFFERENTIATION OF CAUSES OF ABDOMINAL PAIN

(71) Applicant: ASTUTE MEDICAL, INC., San Diego, CA (US)

(72) Inventors: Joseph Anderberg, Encinitas, CA (US); Jeff Gray, Solana Beach, CA (US); Paul McPherson, Encinitas, CA (US); Kevin Nakamura, Cardiff by the Sea, CA (US); James Patrick Kampf, San Diego, CA (US); Thomas Kwan, San Diego, CA (US)

(73) Assignee: Astute Medical, Inc., San Diego, CA (US)

( * ) Notice: Subject to any disclaimer, the term of this patent is extended or adjusted under 35 U.S.C. 154(b) by 879 days.

(21) Appl. No.: 15/023,357

(22) PCT Filed: Sep. 19, 2014

(86) PCT No.: PCT/US2014/056653
§ 371 (c)(1),
(2) Date: Mar. 18, 2016

(87) PCT Pub. No.: WO2015/042465
PCT Pub. Date: Mar. 26, 2015

(65) Prior Publication Data
US 2016/0245824 A1  Aug. 25, 2016

Related U.S. Application Data

(60) Provisional application No. 61/880,765, filed on Sep. 20, 2013.

(51) Int. Cl.
*G01N 33/68* (2006.01)

(52) U.S. Cl.
CPC ..... *G01N 33/6893* (2013.01); *G01N 2800/06* (2013.01); *G01N 2800/52* (2013.01); *G01N 2800/60* (2013.01)

(58) Field of Classification Search
None
See application file for complete search history.

(56) References Cited

U.S. PATENT DOCUMENTS

| | | | |
|---|---|---|---|
| 5,096,670 A * | 3/1992 | Harris | G01N 35/028 356/244 |
| 5,480,792 A | 1/1996 | Buechler et al. | |
| 5,525,524 A | 6/1996 | Buechler et al. | |
| 5,571,698 A | 11/1996 | Ladner et al. | |
| 5,631,171 A | 5/1997 | Sandstrom et al. | |
| 5,679,526 A | 10/1997 | Buechler et al. | |
| 5,824,799 A | 10/1998 | Buechler et al. | |
| 5,851,776 A | 12/1998 | Valkirs | |
| 5,885,527 A | 3/1999 | Buechler et al. | |
| 5,922,615 A | 7/1999 | Nowakowski et al. | |
| 5,939,272 A | 8/1999 | Buechler et al. | |
| 5,947,124 A | 9/1999 | Buechler et al. | |
| 5,955,377 A | 9/1999 | Maul et al. | |
| 5,985,579 A | 11/1999 | Buechler et al. | |
| 6,019,944 A | 2/2000 | Buechler et al. | |
| 6,057,098 A | 5/2000 | Buechler et al. | |
| 6,113,855 A | 9/2000 | Buechler et al. | |
| 6,143,576 A | 11/2000 | Buechler et al. | |
| 2002/0150957 A1 | 10/2002 | Slotman | |
| 2006/0094056 A1* | 5/2006 | Chappell | G01N 33/564 435/7.1 |
| 2006/0292038 A1* | 12/2006 | Johansson | G01N 35/025 422/82.05 |
| 2007/0092911 A1* | 4/2007 | Buechler | G01N 33/6872 435/7.1 |
| 2012/0028268 A1 | 2/2012 | Kentsis et al. | |
| 2012/0115174 A1* | 5/2012 | Pugia | C12Q 1/6883 435/7.92 |
| 2012/0264645 A1* | 10/2012 | Lillard, Jr. | C07K 16/24 506/9 |
| 2013/0122528 A1 | 5/2013 | Tyrell et al. | |
| 2013/0171670 A1 | 7/2013 | Bar-Or et al. | |

FOREIGN PATENT DOCUMENTS

| | | |
|---|---|---|
| CN | 1880958 A | 12/2006 |
| CN | 101124336 A | 2/2008 |
| SU | 1005774 A1 | 3/1983 |
| WO | 2004059293 A2 | 7/2004 |

(Continued)

OTHER PUBLICATIONS

De-Oliveira-Pinto et al., Regulation of Inflammatory Chemokine Receptors on Blood T Cells Associated to the Circulating Versus Liver Chemokines in Dengue Fever, PLoS ONE, 7(7), (2012), p. 1-14 (Year: 2012).*
Cartwright et al., Evaluation of Acute Abdominal Pain in Adults, American Family Physician, 77(7), (2008), p. 971-978. (Year: 2008).*
Heverhagen et al., MR Imaging for Acute Lower Abdominal and Pelvic Pain, RadioGraphics, 29(6), (2009), p. 1781-1797. (Year: 2009).*
International Search Report and Written Opinion issued in PCT/US2014/056653 dated Dec. 30, 2014 (12 pages).

(Continued)

*Primary Examiner* — Ellen J Marcsisin
(74) *Attorney, Agent, or Firm* — Womble Bond Dickinson (US) LLP

(57) ABSTRACT

The present invention relates to methods and compositions for monitoring, diagnosis, prognosis, and determination of treatment regimens in appendicitis patients and in patients at risk for appendicitis. In particular, the invention relates to using assays that detect one or more biomarkers as diagnostic and prognostic biomarker assays in such patients.

15 Claims, No Drawings

(56) References Cited

FOREIGN PATENT DOCUMENTS

| WO | WO-2006073682 A2 | * | 7/2006 | ......... G01N 33/6863 |
| WO | WO-2008118798 A1 | * | 10/2008 | ....... G01N 33/57449 |
| WO | WO-2010078411 A1 | * | 7/2010 | ......... G01N 33/6893 |
| WO | 2013027823 A1 | | 3/2015 | |

OTHER PUBLICATIONS

Extended European Search Report and Written Opinion issued in EP 14845927 dated Jun. 20, 2017, (12 pages).
Office Action issued by SIPO in Chinese patent application No. 2014800514696 dated Nov. 9, 2017—incl Engl lang transl, (22 pages).
Cwirla et al., Peptides on phage: A vast library of peptides for identifying ligands. Proc Natl Acad Sci U S A. Aug. 1990;87(16):6378-6382.
Devlin et al., Random peptide libraries: a source of specific protein binding molecules. Science. Jul. 27, 1990;249(4967):404-406.
Fischer et al., A readers' guide to the interpretation of diagnostic test properties: clinical example of sepsis. Intensive Care Med. Jul. 2003;29(7):1043-1051.
Glucagon-Like Peptide-1 (Active) ELISA Kit, 96-Well Plate (Cat. #ELP-35K). EMD Millipore catalogue. Rev date: Mar. 12, 2012, accessed online at:http://www.sceti.jp/images/psearch/pdf/LIN_EGLP-35K_p.pdf (14 pages).
Kentsis et al., Discovery and Validation of Urine Markers of Acute Pediatric Appendicitis Using High-Accuracy Mass Spectrometry. Ann Emerg Med. Jan. 2010;55(1):62-70.e4.
Kharbanda et al., Novel Serum and Urine Markers for Pediatric Appendicitis. Acad Emerg Med. Jan. 2012;19(1):56-62.
Murphy et al., Acute appendicitis is characterized by a uniform and highly selective pattern of inflammatory gene expression. Mucosal Immunol. Jul. 2008;1(4):297-308.
Nelson and Griswold, A computer program for calculating antibody affinity constants. Comput Methods Programs Biomed. Jul.-Aug. 1988;27(1):65-68.
Scott and Smith, Searching for peptide ligands with an epitope library. Science. Jul. 27, 1990;249(4967):386-388.
Van ERP et al., Application of a sol particle immunoassay to the determination of affinity constants of monoclonal antibodies. J Immunoassay. 1991;12(3):425-443.
Ward et al., Binding activities of a repertoire of single immunoglobulin variable domains secreted from *Escherichia coli*. Nature. Oct. 12, 1989;341(6242):544-546.
Wilson et al., Simplified conjugation chemistry for coupling peptides to F(ab') fragments: autologous red cell agglutination assay for HIV-1 antibodies. J Immunol Methods. Oct. 14, 1994;175(2):267-273.
Yarmush et al., Coupling of antibody-binding fragments to solid-phase supports: site-directed binding of F(ab')2 fragments. J Biochem Biophys Methods. Dec. 1992;25(4):285-297.
YK160 GLP-1 EIA Kit for Measurement of Rat, Mouse & Human GLP-1. Yanaihara Institute Inc. 2009, accessed online at: http://www.yanaihara-inc.com/englishdata/kit_manual-absNK160_GLP-1-abs.pdf (10 pages).
Office Action issued by SIPO in Chinese patent application No. 201480051469.6 dated Mar. 13, 2017—incl Engl lang transl, (48 pages).
Partial Supplementary European Search Report issued in EP 14845927 dated Mar. 13, 2017, (9 pages).
Hennelly and Bachur, Appendicitis update. Curr Opin Pediatr. Jun. 2011;23(3):281-285.
Mortensen et al., GLP-I and GIP are colocalized in a subset of endocrine cells in the small intestine. Regul Pept. Jul. 15, 2003;114(2-3):189-196.
Ozguner et al., Are Neutrophil CD64 Expression and Interleukin-6 Early Useful Markers for Diagnosis of Acute Appendicitis? Eur J Pediatr Surg. Apr. 2014;24(2):179-183.
Wu et al., Evaluation of high mobility group box 1 protein as a presurgical diagnostic marker reflecting the severity of acute appendicitis. Scand J Trauma Resusc Emerg Med. Sep. 4, 2012;20:61.
Yu et al., Systematic review and meta-analysis of the diagnostic accuracy of procalcitonin, C-reactive protein and white blood cell count for suspected acute appendicitis. Br J Surg. Feb. 2013;100(3):322-329.

* cited by examiner

METHODS AND COMPOSITIONS FOR DIAGNOSIS AND PROGNOSIS OF APPENDICITIS AND DIFFERENTIATION OF CAUSES OF ABDOMINAL PAIN

The present invention is filed under 35 U.S.C. § 371 as the U.S. national phase of International Application No. PCT/US2014/056653, filed Sept. 19, 2014, which claims priority from U.S. Provisional patent application Ser. No., 61/880,765 filed Sept. 20, 2013, each of which is hereby incorporated in its entirety including all tables, figures and claims.

BACKGROUND OF THE INVENTION

The following discussion of the background of the invention is merely provided to aid the reader in understanding the invention and is not admitted to describe or constitute prior art to the present invention.

Acute appendicitis is an inflammatory condition which typically results from a primary obstruction of the appendix lumen. Once obstructed, the appendix subsequently swells, increasing pressures within the lumen and the walls of the appendix, resulting in thrombosis and occlusion of the small vessels, and stasis of lymphatic flow. The causative agents of appendicitis include foreign bodies, trauma, intestinal worms, lymphadenitis, and, most commonly, calcified fecal deposits known as appendicoliths or fecaliths. Diagnosis is based on patient history, symptoms and physical examination. Typical appendicitis usually includes abdominal pain beginning in the region of the umbilicus for several hours, associated with anorexia, nausea or vomiting. The pain typically settles into the right lower quadrant.

A commonly used acronym for diagnosis is PALF: pain, anorexia, leukocytosis, and fever. Atypical histories lack this typical progression and may include pain in the right lower quadrant as an initial symptom. Atypical histories often require imaging with ultrasound and/or CT scanning. Blood tests for appendicitis are normal, and so not diagnostic, in about 50% of cases. These tests tend to be relatively simple. An abnormal rise in the number of white blood cells in the blood is a crude indicator of infection or inflammation going on in the body. Such a rise is not specific to appendicitis alone. If it is abnormally elevated, with a good history and examination findings pointing towards appendicitis, the likelihood of having the disease is higher. Imaging tests such as CT, while useful, expose the recipient to diagnostic levels of radiation.

In terms of biomarkers, C-reactive protein (CRP), an acute-phase response protein produced by the liver in response to inflammatory processes, as been used by clinicians. Likewise, other general inflammatory markers such as procalcitonin, Interleukin-6 (IL-6), Interleukin-8 (IL-8), high mobility group box-1 protein (HMGB1) S100A8/A9, etc., have been studied by clinicians. Like the number of white blood cells, however, these are not specific biomarkers of appendicitis, and so exhibit poor specificity in use. Leucine-rich alpha-2-glycoprotein (LRG) was recently suggested to be a more specific indicator of appendicitis in a pediatric population. Kentsis et al., Ann. Emerg. Med. 55: 62-70.e4. Epub 2009 Jun. 25; Kharbanda et al., Academic Emerg. Med. 19: 56-62, 2012.

There remains a need in the art for a rapid, objective, clinically accurate, available diagnostic tool for aiding in the diagnosis and care of appendicitis.

BRIEF SUMMARY OF THE INVENTION

The present invention relates to the identification and use of diagnostic markers for appendicitis. The methods and compositions described herein can meet the need in the art for rapid, sensitive and specific diagnostic assay to be used in the diagnosis and differentiation of abdominal pain and the identification of appendicitis. In various aspects, the invention relates to materials and procedures for identifying markers that are associated with the diagnosis, prognosis, or differentiation of appendicitis in a patient; to using such markers in diagnosing and treating a patient and/or to monitor the course of a treatment regimen; to using such markers to identify subjects at risk for one or more adverse outcomes related to appendicitis; and for screening compounds and pharmaceutical compositions that might provide a benefit in treating or preventing such conditions.

In a first aspect, the invention discloses methods for determining a diagnosis or prognosis related to appendicits, or for differentiating between causes of abdominal pain. As described herein, measurement of one or more biomarkers selected from the group consisting of 72 kDa type IV collagenase, Adiponectin, Advanced glycosylation end product-specific receptor, Alpha-2 macroglobulin, Alpha-2-HS-glycoprotein, Alpha-fetoprotein, Angiopoietin-1, Anti-leukoproteinase, Apolipoprotein(a), Cancer Antigen 15-3, Cancer Antigen 19-9, Carbonic anhydrase 9, Carcinoembryonic antigen-related cell adhesion molecule 5, C-C motif chemokine 1, C-C motif chemokine 13, C-C motif chemokine 15, C-C motif chemokine 17, C-C motif chemokine 19, C-C motif chemokine 20, C-C motif chemokine 21, C-C motif chemokine 22, C-C motif chemokine 23, C-C motif chemokine 24, C-C motif chemokine 26, C-C motif chemokine 27, C-C motif chemokine 3, C-C motif chemokine 4, C-C motif chemokine 7, C-C motif chemokine 8, Ceruloplasmin, Choriogonadotropin subunit beta, Collagenase 3, C-Peptide, Creatine Kinase-MB, C-X-C motif chemokine 10, C-X-C motif chemokine 11, C-X-C motif chemokine 13, C-X-C motif chemokine 16, C-X-C motif chemokine 5, C-X-C motif chemokine 6, C-X-C motif chemokine 9, Cystatin-C, Endothelial protein C receptor, Eotaxin, Epidermal growth factor receptor, Ferritin, Fibrinogen, Gastric inhibitory polypeptide, Glucagon, Glucagon-like peptide 1, Granulocyte-macrophage colony-stimulating factor, Growth-regulated alpha, beta, and gamma proteins, Heparin-binding growth factor 2, Hepatocyte growth factor, Immunoglobulin A, Immunoglobulin M, Immunoglogulin G1, Immunoglogulin G2, Immunoglogulin G3, Immunoglogulin G4, Insulin, Insulin-like growth factor-binding protein 1, Insulin-like growth factor-binding protein 2, Insulin-like growth factor-binding protein 3, Insulin-like growth factor-binding protein 4, Insulin-like growth factor-binding protein 5, Insulin-like growth factor-binding protein 6, Insulin-like growth factor-binding protein 7, Interferon alpha-2, Interferon gamma, Interleukin-1 alpha, Interleukin-1 beta, Interleukin-1 receptor antagonist protein, Interleukin-1 receptor type I, Interleukin-1 receptor type II, Interleukin-11, Interleukin-12, Interleukin-12 subunit beta, Interleukin-13, Interleukin-15, Interleukin-2, Interleukin-20, Interleukin-21, Interleukin-23, Interleukin-28A, Interleukin-29, Interleukin-3, Interleukin-33, Interleukin-4, Interleukin-5, Interleukin-6 receptor subunit alpha, Interleukin-6 receptor subunit beta, Interleukin-7, Interleukin-9, Interstitial collagenase, Islet amyloid polypeptide, Keratin, type I cytoskeletal 19 (aa311-367), Kit ligand, Leptin, Leukemia inhibitory factor, Lymphotactin, Lymphotoxin-alpha, Macrophage colony-stimulating factor 1, Macrophage metalloelastase, Macrophage migration inhibitory factor, Matrilysin, Metalloproteinase inhibitor 1, Metalloproteinase inhibitor 2, Metalloproteinase inhibitor 3, Metalloproteinase inhibitor 4, Myoglobin, Pancreatic prohormone, Peptide YY, Pro-epidermal growth factor, Pro-interleukin-16, Prolactin, Prostate-specific antigen, Protein S100-A12, Protransforming growth factor alpha, Secretory immunoglobulin A, Serum amyloid P-component, SL cytokine, Stromal cell-derived factor 1, Stromelysin-1, Thrombopoietin, Thymic stromal lymphopoietin, Tumor necrosis factor, Tumor necrosis factor ligand superfamily member 10, Tumor necrosis factor ligand superfamily member 6, Tumor necrosis factor receptor superfamily member 1A, Tumor necrosis factor receptor superfamily member 1B, Vascular endothelial growth factor receptor 1, Vascular endothelial growth factor receptor 2, Vascular endothelial growth factor receptor 3, von Willebrand Factor, and WAP four-disulfide core domain protein 2 (each referred to herein for convenience as an "appendicitis biomarker") can be used for diagnosis, prognosis, risk stratification, monitoring, categorizing and determination of further diagnosis and treatment regimens in patients having or suspected of having appendicitis. The appendicitis biomarkers of the present invention may be used, individually or in panels comprising a plurality of appendicitis biomarkers. The presence or amount of such marker(s) in a sample obtained from the subject can be used to rule in or rule out appendicitis, and to monitor subjects for improving or worsening conditions related to appendicitis.

In a first aspect, the present invention relates to methods for evaluating an appendicitis patient or a patient being evaluated for a possible diagnosis. These methods comprise performing an assay method that is configured to detect one or more biomarkers selected from the group consisting of 72 kDa type IV collagenase, Adiponectin, Advanced glycosylation end product-specific receptor, Alpha-2 macroglobulin, Alpha-2-HS-glycoprotein, Alpha-fetoprotein, Angiopoietin-1, Antileukoproteinase, Apolipoprotein(a), Cancer Antigen 15-3, Cancer Antigen 19-9, Carbonic anhydrase 9, Carcinoembryonic antigen-related cell adhesion molecule 5, C-C motif chemokine 1, C-C motif chemokine 13, C-C motif chemokine 15, C-C motif chemokine 17, C-C motif chemokine 19, C-C motif chemokine 20, C-C motif chemokine 21, C-C motif chemokine 22, C-C motif chemokine 23, C-C motif chemokine 24, C-C motif chemokine 26, C-C motif chemokine 27, C-C motif chemokine 3, C-C motif chemokine 4, C-C motif chemokine 7, C-C motif chemokine 8, Ceruloplasmin, Choriogonadotropin subunit beta, Collagenase 3, C-Peptide, Creatine Kinase-MB, C-X-C motif chemokine 10, C-X-C motif chemokine 11, C-X-C motif chemokine 13, C-X-C motif chemokine 16, C-X-C motif chemokine 5, C-X-C motif chemokine 6, C-X-C motif chemokine 9, Cystatin-C, Endothelial protein C receptor, Eotaxin, Epidermal growth factor receptor, Ferritin, Fibrinogen, Gastric inhibitory polypeptide, Glucagon, Glucagon-like peptide 1, Granulocyte-macrophage colony-stimulating factor, Growth-regulated alpha, beta, and gamma proteins, Heparin-binding growth factor 2, Hepatocyte growth factor, Immunoglobulin A, Immunoglobulin M, Immunoglogulin G1, Immunoglogulin G2, Immunoglogulin G3, Immunoglogulin G4, Insulin, Insulin-like growth factor-binding protein 1, Insulin-like growth factor-binding protein 2, Insulin-like growth factor-binding protein 3, Insulin-like growth factor-binding protein 4, Insulin-like growth factor-binding protein 5, Insulin-like growth factor-binding protein 6, Insulin-like growth factor-binding protein 7, Interferon alpha-2, Interferon gamma, Interleukin-1 alpha, Interleukin-1 beta, Interleukin-1 receptor antagonist protein, Interleukin-1 receptor type I, Interleukin-1 receptor type II, Interleukin-11, Interleukin-12, Interleukin-12 subunit beta, Interleukin-13, Interleukin-15, Interleukin-2, Interleukin-20, Interleukin-21, Interleukin-23, Interleukin-28A, Interleukin-29, Interleukin-3, Interleukin-33, Interleukin-4, Interleukin-5, Interleukin-6 receptor subunit alpha, Interleukin-6 receptor subunit beta, Interleukin-7, Interleukin-9, Interstitial collagenase, Islet amyloid polypeptide, Keratin, type I cytoskeletal 19 (aa311-367), Kit ligand, Leptin, Leukemia inhibitory factor, Lymphotactin, Lymphotoxin-alpha, Macrophage colony-stimulating factor 1, Macrophage metalloelastase, Macrophage migration inhibitory factor, Matrilysin, Metalloproteinase inhibitor 1, Metalloproteinase inhibitor 2, Metalloproteinase inhibitor 3, Metalloproteinase inhibitor 4, Myoglobin, Pancreatic prohormone, Peptide YY, Pro-epidermal growth factor, Pro-interleukin-16, Prolactin, Prostate-specific antigen, Protein S100-A12, Protransforming growth factor alpha, Secretory immunoglobulin A, Serum amyloid P-component, SL cytokine, Stromal cell-derived factor 1, Stromelysin-1, Thrombopoietin, Thymic stromal lymphopoietin, Tumor necrosis factor, Tumor necrosis factor ligand superfamily member 10, Tumor necrosis factor ligand superfamily member 6, Tumor necrosis factor receptor superfamily member 1A, Tumor necrosis factor receptor superfamily member 1B, Vascular endothelial growth factor receptor 1, Vascular endothelial growth factor receptor 2, Vascular endothelial growth factor receptor 3, von Willebrand Factor, and WAP four-disulfide core domain protein 2, the results of which assay(s) is/are then correlated to the status of the patient. This correlation to status may include one or more of the following: diagnosis of acute appendicitis; indication of a prognosis resulting from acute appendicitis. For convenience, patients being evaluated in this manner are referred to herein as "appendicitis patients," whether or not the appendicitis diagnosis has been confirmed at the time of the evaluation.

In certain embodiments, the methods for evaluating a patient described herein are methods for risk stratification of the patient; that is, assigning a likelihood of one or more future changes in health status to the patient. In these embodiments, the assay result(s) is/are correlated to one or more such future changes. A level or a change in level of one or more appendicitis biomarkers, which in turn is(are) associated with an increased probability of morbidity or death, is referred to as being "associated with an increased predisposition to an adverse outcome" in a patient.

In such risk stratification embodiments, preferably the likelihood or risk assigned is that an event of interest is more or less likely to occur within 180 days of the time at which the body fluid sample is obtained from the appendicitis patient. In particularly preferred embodiments, the likelihood or risk assigned relates to an event of interest occurring within a shorter time period such as 18 months, 120 days, 90 days, 60 days, 45 days, 30 days, 21 days, 14 days, 7 days, 5 days, 96 hours, 72 hours, 48 hours, 36 hours, 24 hours, 12 hours, or less. A risk at 0 hours of the time at which the body fluid sample is obtained from the appendicitis patient is equivalent to diagnosis of a current condition.

For a positive going marker, an increased likelihood of the occurrence of a diagnosis is assigned to the patient when the measured concentration is above the threshold (relative to the likelihood assigned when the measured concentration is below the threshold); alternatively, when the measured concentration is below the threshold, an increased likelihood of the nonoccurrence of a diagnosis may be assigned to the patient (relative to the likelihood assigned when the measured concentration is above the threshold). For a negative going marker, an increased likelihood of the occurrence of a diagnosis is assigned to the patient when the measured concentration is below the threshold (relative to the likelihood assigned when the measured concentration is above the threshold); alternatively, when the measured concentration is above the threshold, an increased likelihood of the non-occurrence of a diagnosis may be assigned to the patient (relative to the likelihood assigned when the measured concentration is below the threshold).

In certain embodiments, a biomarker or panel of biomarkers is correlated to a condition or disease by merely its presence or absence. In other embodiments, a threshold level of a diagnostic or prognostic indicator can be established, and the level of the indicator in a patient sample can simply be compared to the threshold level. A variety of methods may be used by the skilled artisan to arrive at a desired threshold value for use in these methods. For example, for a positive going marker the threshold value may be determined from a population of patients not having acute appendicitis by selecting a concentration representing the $75^{th}$, $85^{th}$, $90^{th}$, $95^{th}$, or $99^{th}$ percentile of an appendicitis biomarker or biomarkers measured in such "normal" patients. Alternatively, the threshold value may be determined from a "diseased" population of patients by selecting a concentration representing the $75^{th}$, $85^{th}$, $90^{th}$, $95^{th}$, or $99^{th}$ percentile of a biomarker or biomarkers measured in patients suffering from acute appendicitis.

Alternatively, the threshold value may be determined from a "diseased" population of appendicitis patients having a predisposition for an outcome such as death, worsening disease, etc.), by selecting a concentration representing the $75^{th}$, $85^{th}$, $90^{th}$, $95^{th}$, or $99^{th}$ percentile of a biomarker or biomarkers measured in patients suffering from acute appendicitis and who later suffered from the outcome of interest.

In another alternative, the threshold value may be determined from a prior measurement of a biomarker or biomarkers in the same patient; that is, a temporal change in the level of a biomarker or biomarkers in the same patient may be used to assign a diagnosis or a prognosis to the patient. For example, a diagnostic indicator may be determined at an initial time, and again at a second time. In such embodiments, an increase in the marker from the initial time to the second time may be diagnostic of appendicitis or a given prognosis.

The foregoing discussion is not meant to imply, however, that the appendicitis biomarkers of the present invention must be compared to corresponding individual thresholds. Methods for combining assay results can comprise the use of multivariate logistical regression, loglinear modeling, neural network analysis, n-of-m analysis, decision tree analysis, calculating ratios of markers, etc. This list is not meant to be limiting. In these methods, a composite result which is determined by combining individual markers may be treated as if it is itself a marker; that is, a threshold may be determined for the composite result as described herein for individual markers, and the composite result for an individual patient compared to this threshold.

The ability of a particular test to distinguish two populations can be established using ROC analysis. For example, ROC curves established from a "first" subpopulation which has a particular disease (or which is predisposed to some outcome), and a "second" subpopulation which does not have the disease (or is not so predisposed) can be used to calculate a ROC curve, and the area under the curve provides a measure of the quality of the test. Preferably, the tests described herein provide a ROC curve area greater than 0.5, preferably at least 0.6, more preferably 0.7, still more preferably at least 0.8, even more preferably at least 0.9, and most preferably at least 0.95.

In certain aspects, the measured concentration of one or more appendicitis biomarkers, or a composite of such markers, may be treated as continuous variables. For example, any particular concentration can be converted into a corresponding probability of existing disease, of a future outcome for the appendicitis patient, or mortality, of a SIRS classification, etc. In yet another alternative, a threshold that can provide an acceptable level of specificity and sensitivity in separating a population of appendicitis patients into "bins" such as a "first" subpopulation and a "second" subpopulation. A threshold value is selected to separate this first and second population by one or more of the following measures of test accuracy:

an odds ratio greater than 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less;

a specificity of greater than 0.5, preferably at least about 0.6, more preferably at least about 0.7, still more preferably at least about 0.8, even more preferably at least about 0.9 and most preferably at least about 0.95, with a corresponding sensitivity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

a sensitivity of greater than 0.5, preferably at least about 0.6, more preferably at least about 0.7, still more preferably at least about 0.8, even more preferably at least about 0.9 and most preferably at least about 0.95, with a corresponding specificity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

at least about 75% sensitivity, combined with at least about 75% specificity;

a positive likelihood ratio (calculated as sensitivity/(1−specificity)) of greater than 1, at least about 2, more preferably at least about 3, still more preferably at least about 5, and most preferably at least about 10; or a negative likelihood ratio (calculated as (1-sensitivity)/specificity) of less than 1, less than or equal to about 0.5, more preferably less than or equal to about 0.3, and most preferably less than or equal to about 0.1.

The term "about" in the context of any of the above measurements refers to +/−5% of a given measurement.

Multiple thresholds may also be used to assess a patient. For example, a "first" subpopulation identified by an existing disease, predisposition to a future outcome for the appendicitis patient, predisposition to mortality, etc., and a "second" subpopulation which is not so predisposed can be combined into a single group. This group is then subdivided into three or more equal parts (known as tertiles, quartiles, quintiles, etc., depending on the number of subdivisions). An odds ratio is assigned to appendicitis patients based on which subdivision they fall into. If one considers a tertile, the lowest or highest tertile can be used as a reference for comparison of the other subdivisions. This reference subdivision is assigned an odds ratio of 1. The second tertile is assigned an odds ratio that is relative to that first tertile. That is, someone in the second tertile might be 3 times more likely to suffer one or more future changes in disease status in comparison to someone in the first tertile. The third tertile is also assigned an odds ratio that is relative to that first tertile.

In certain embodiments, the assay method is an immunoassay. Antibodies for use in such assays will specifically bind a full length appendicitis biomarker of interest, and may also bind one or more polypeptides that are "related" thereto, as that term is defined hereinafter. Numerous immunoassay formats are known to those of skill in the art. Preferred body fluid samples are selected from the group consisting of urine, blood, serum, saliva, tears, and plasma.

The foregoing method steps should not be interpreted to mean that the appendicitis biomarker assay result(s) is/are used in isolation in the methods described herein. Rather, additional variables or other clinical indicia may be included in the methods described herein. For example, a risk stratification, diagnostic, classification, monitoring, etc. method may combine the assay result(s) with one or more variables measured for the appendicitis patient selected from the group consisting of demographic information (e.g., weight, sex, age, race), clinical variables (e.g., blood pressure, temperature, respiration rate), risk scores (Alvarado score, Pediatric Appendicitis Score, etc.). This list is not meant to be limiting.

When more than one marker is measured, the individual markers may be measured in samples obtained at the same time, or may be determined from samples obtained at different (e.g., an earlier or later) times. The individual markers may also be measured on the same or different body fluid samples. For example, one appendicitis biomarker may be measured in a serum or plasma sample and another appendicitis biomarker may be measured in a urine sample. In addition, assignment of a likelihood may combine an individual biomarker assay result with temporal changes in one or more additional variables.

In various related aspects, the present invention also relates to devices and kits for performing the methods described herein. Suitable kits comprise reagents sufficient for performing an assay for at least one of the described appendicitis biomarkers, together with instructions for performing the described threshold comparisons.

In certain embodiments, reagents for performing such assays are provided in an assay device, and such assay devices may be included in such a kit. Preferred reagents may comprise one or more solid phase antibodies, the solid phase antibody comprising antibody that detects the intended biomarker target(s) bound to a solid support. In the case of sandwich immunoassays, such reagents can also include one or more detectably labeled antibodies, the detectably labeled antibody comprising antibody that detects the intended biomarker target(s) bound to a detectable label. Additional optional elements that may be provided as part of an assay device are described hereinafter.

Detectable labels may include molecules that are themselves detectable (e.g., fluorescent moieties, electrochemical labels, ecl (electrochemical luminescence) labels, metal chelates, colloidal metal particles, etc.) as well as molecules that may be indirectly detected by production of a detectable reaction product (e.g., enzymes such as horseradish peroxidase, alkaline phosphatase, etc.) or through the use of a specific binding molecule which itself may be detectable (e.g., a labeled antibody that binds to the second antibody, biotin, digoxigenin, maltose, oligohistidine, 2,4-dintrobenzene, phenylarsenate, ssDNA, dsDNA, etc.).

Generation of a signal from the signal development element can be performed using various optical, acoustical, and electrochemical methods well known in the art. Examples of detection modes include fluorescence, radiochemical detection, reflectance, absorbance, amperometry, conductance, impedance, interferometry, ellipsometry, etc. In certain of these methods, the solid phase antibody is coupled to a transducer (e.g., a diffraction grating, electrochemical sensor, etc) for generation of a signal, while in others, a signal is generated by a transducer that is spatially separate from the solid phase antibody (e.g., a fluorometer that employs an excitation light source and an optical detector). This list is not meant to be limiting. Antibody-based biosensors may also be employed to determine the presence or amount of analytes that optionally eliminate the need for a labeled molecule.

DETAILED DESCRIPTION OF THE INVENTION

The present invention relates to methods and compositions for diagnosis, differential diagnosis, risk stratification, monitoring, classifying and determination of treatment regimens in patients diagnosed with, or at risk of, appendicitis. In various embodiments, a measured concentration of one or more biomarkers selected from the group consisting of 72 kDa type IV collagenase, Adiponectin, Advanced glycosylation end product-specific receptor, Alpha-2 macroglobulin, Alpha-2-HS-glycoprotein, Alpha-fetoprotein, Angiopoietin-1, Antileukoproteinase, Apolipoprotein(a), Cancer Antigen 15-3, Cancer Antigen 19-9, Carbonic anhydrase 9, Carcinoembryonic antigen-related cell adhesion molecule 5, C-C motif chemokine 1, C-C motif chemokine 13, C-C motif chemokine 15, C-C motif chemokine 17, C-C motif chemokine 19, C-C motif chemokine 20, C-C motif chemokine 21, C-C motif chemokine 22, C-C motif chemokine 23, C-C motif chemokine 24, C-C motif chemokine 26, C-C motif chemokine 27, C-C motif chemokine 3, C-C motif chemokine 4, C-C motif chemokine 7, C-C motif chemokine 8, Ceruloplasmin, Choriogonadotropin subunit beta, Collagenase 3, C-Peptide, Creatine Kinase-MB, C-X-C motif chemokine 10, C-X-C motif chemokine 11, C-X-C motif chemokine 13, C-X-C motif chemokine 16, C-X-C motif chemokine 5, C-X-C motif chemokine 6, C-X-C motif chemokine 9, Cystatin-C, Endothelial protein C receptor, Eotaxin, Epidermal growth factor receptor, Ferritin, Fibrinogen, Gastric inhibitory polypeptide, Glucagon, Glucagon-like peptide 1, Granulocyte-macrophage colony-stimulating factor, Growth-regulated alpha, beta, and gamma proteins, Heparin-binding growth factor 2, Hepatocyte growth factor, Immunoglobulin A, Immunoglobulin M, Immunoglogulin G1, Immunoglogulin G2, Immunoglogulin G3, Immunoglogulin G4, Insulin, Insulin-like growth factor-binding protein 1, Insulin-like growth factor-binding protein 2, Insulin-like growth factor-binding protein 3, Insulin-like growth factor-binding protein 4, Insulin-like growth factor-binding protein 5, Insulin-like growth factor-binding protein 6, Insulin-like growth factor-binding protein 7, Interferon alpha-2, Interferon gamma, Interleukin-1 alpha, Interleukin-1 beta, Interleukin-1 receptor antagonist protein, Interleukin-1 receptor type I, Interleukin-1 receptor type II, Interleukin-11, Interleukin-12, Interleukin-12 subunit beta, Interleukin-13, Interleukin-15, Interleukin-2, Interleukin-20, Interleukin-21, Interleukin-23, Interleukin-28A, Interleukin-29, Interleukin-3, Interleukin-33, Interleukin-4, Interleukin-5, Interleukin-6 receptor subunit alpha, Interleukin-6 receptor subunit beta, Interleukin-7, Interleukin-9, Interstitial collagenase, Islet amyloid polypeptide, Keratin, type I cytoskeletal 19 (aa311-367), Kit ligand, Leptin, Leukemia inhibitory factor, Lymphotactin, Lymphotoxin-alpha, Macrophage colony-stimulating factor 1, Macrophage metalloelastase, Macrophage migration inhibitory factor, Matrilysin, Metalloproteinase inhibitor 1, Metalloproteinase inhibitor 2, Metalloproteinase inhibitor 3, Metalloproteinase inhibitor 4, Myoglobin, Pancreatic prohormone, Peptide YY, Pro-epidermal growth factor, Pro-interleukin-16, Prolactin, Prostate-specific antigen, Protein S100-A12, Protransforming growth factor alpha, Secretory immunoglobulin A, Serum amyloid P-component, SL cytokine, Stromal cell-derived factor 1, Stromelysin-1, Thrombopoietin, Thymic stromal lymphopoietin, Tumor necrosis factor, Tumor necrosis factor ligand superfamily member 10, Tumor necrosis factor ligand superfamily member 6, Tumor necrosis factor receptor superfamily member 1A, Tumor necrosis factor receptor superfamily member 1B, Vascular endothelial growth factor receptor 1, Vascular endothelial growth factor receptor 2, Vascular endothelial growth factor receptor 3, von Willebrand Factor, and WAP four-disulfide core domain protein 2 or one or more markers related thereto, are correlated to the status of the patient. As described herein, measurement of one or more biomarkers of the present invention may be used, individually or in panels comprising a plurality of biomarkers, in methods and compositions for the diagnosis, prognosis, or differentiation of abdominal pain in order to rule in or out appendicitis and/or a particular outcome. Such markers can be used in diagnosing and treating a subject and/or to monitor the course of a treatment regimen; for screening subjects for the occurrence or risk of a particular disease; and for screening compounds and pharmaceutical compositions that might provide a benefit in treating or preventing such conditions.

For purposes of this document, the following definitions apply:

The term "subject" as used herein refers to a human or non-human organism. Thus, the methods and compositions described herein are applicable to both human and veterinary disease. Further, while a subject is preferably a living organism, the invention described herein may be used in post-mortem analysis as well. Preferred subjects are humans, and most preferably "patients," which as used herein refers to living humans that are receiving medical care for a disease or condition. This includes persons with no defined illness who are being investigated for signs of pathology. An "appendicitis patient" is a patient exhibiting symptoms consistent with appendicitis and being evaluated for its presence, absence, or outcome Conditions within the differential diagnosis include gallbladder attack, kidney infection, pneumonia, rheumatic fever, diabetic ketoacidosis, ectopic pregnancy, twisted ovarian cyst, hemorrhaging ovarian follicle, urinary tract infection, ulcerative colitis, pancreatitis, intestinal obstruction, pelvic inflammatory disease, diverticulitis, carcinoma of the colon, and aortic aneurysm. In preferred embodiments, the biomarkers of the present invention distinguish appendicitis from one or more of these mimicking conditions.

Preferably, an analyte such as an appendicitis biomarker is measured in a sample. Such a sample may be obtained from a patient, such as an appendicitis patient. Preferred samples are body fluid samples.

The term "body fluid sample" as used herein refers to a sample of bodily fluid obtained for the purpose of diagnosis, prognosis, classification or evaluation of an appendicitis patient of interest, such as a patient or transplant donor. In certain embodiments, such a sample may be obtained for the purpose of determining the outcome of an ongoing condition or the effect of a treatment regimen on a condition. Preferred body fluid samples include blood, serum, plasma, urine, saliva, sputum, and pleural effusions. In addition, one of skill in the art would realize that certain body fluid samples would be more readily analyzed following a fractionation or purification procedure, for example, separation of whole blood into serum or plasma components.

The term "diagnosis" as used herein refers to methods by which the skilled artisan can estimate and/or determine the probability ("a likelihood") of whether or not a patient is suffering from a given disease or condition. In the case of the present invention, "diagnosis" includes using the results of an assay, most preferably an immunoassay, for an appendicitis biomarker of the present invention, optionally together with other clinical characteristics, to arrive at a diagnosis (that is, the occurrence or nonoccurrence) of a disease or condition. That such a diagnosis is "determined" is not meant to imply that the diagnosis is 100% accurate. Many biomarkers are indicative of multiple conditions. The skilled clinician does not use biomarker results in an informational vacuum, but rather test results are used together with other clinical indicia to arrive at a diagnosis. Thus, a measured biomarker level on one side of a predetermined diagnostic threshold indicates a greater likelihood of the occurrence of disease in the appendicitis patient relative to a measured level on the other side of the predetermined diagnostic threshold.

Similarly, a prognostic risk signals a probability ("a likelihood") that a given course or outcome will occur. A level or a change in level of a prognostic indicator, which in turn is associated with an increased probability of morbidity or mortality is referred to as being "indicative of an increased likelihood" of an adverse outcome in a patient.

As used herein, the term "relating a signal to the presence or amount" of an analyte reflects the following understanding. Assay signals are typically related to the presence or amount of an analyte through the use of a standard curve calculated using known concentrations of the analyte of interest. As the term is used herein, an assay is "configured to detect" an analyte if an assay can generate a detectable signal indicative of the presence or amount of a physiologically relevant concentration of the analyte. Because an antibody epitope is on the order of 8 amino acids, an immunoassay configured to detect a marker of interest will also detect polypeptides related to the marker sequence, so long as those polypeptides contain the epitope(s) necessary to bind to the antibody or antibodies used in the assay. The term "related marker" as used herein with regard to a biomarker such as one of the appendicitis biomarkers described herein refers to one or more fragments, variants, etc., of a particular marker or its biosynthetic parent that may be detected as a surrogate for the marker itself or as independent biomarkers. The term also refers to one or more polypeptides present in a biological sample that are derived from the biomarker precursor complexed to additional species, such as binding proteins, receptors, heparin, lipids, sugars, etc.

In this regard, the skilled artisan will understand that the signals obtained from an immunoassay are a direct result of complexes formed between one or more antibodies and the target biomolecule (i.e., the analyte) and polypeptides containing the necessary epitope(s) to which the antibodies bind. While such assays may detect the full length biomarker and the assay result be expressed as a concentration of a biomarker of interest, the signal from the assay is actually a result of all such "immunoreactive" polypeptides present in the sample. Expression of biomarkers may also be determined by means other than immunoassays, including protein measurements (such as dot blots, western blots, chromatographic methods, mass spectrometry, etc.) and nucleic acid measurements (mRNA quantitation). This list is not meant to be limiting. With regard to biomarkers which exist in one form as type-I, type-II, or GPI-anchored membrane proteins, such membrane proteins typically comprise a substantial extracellular domain, some or all of which can be detected as soluble forms present in aqueous samples such as blood, serum, plasma, urine, etc., either as cleavage products or as splice variants which delete an effective membrane spanning domain. Preferred assays detect soluble forms of these biomarkers.

The term "positive going" marker as that term is used herein refer to a marker that is determined to be elevated in patients suffering from a disease or condition, relative to those not suffering from that disease or condition. The term "negative going" marker as that term is used herein refer to a marker that is determined to be reduced in patients suffering from a disease or condition, relative to patients not suffering from that disease or condition.

Appendicitis Biomarkers

The following table provides a list of the biomarkers of the present invention, together with the Swiss-Prot entry number for the human precursor. As noted above, these biomarkers are referred to for convenience herein as "appendicitis biomarkers."

| SwissProtNum | Preferred Name |
|---|---|
| Q15848 | Adiponectin |
| Q15109 | Advanced glycosylation end product-specific receptor |
| P01023 | Alpha-2 macroglobulin |
| P02765 | Alpha-2-HS-glycoprotein |
| P02771 | Alpha-fetoprotein |
| Q15389 | Angiopoietin-1 |
| P03973 | Antileukoproteinase |
| P08519 | Apolipoprotein(a) |
| P15941 | Cancer Antigen 15-3 |
| N/A | Cancer Antigen 19-9 |
| Q16790 | Carbonic anhydrase 9 |
| P06731 | Carcinoembryonic antigen-related cell adhesion molecule 5 |
| P22362 | C-C motif chemokine 1 |
| Q99616 | C-C motif chemokine 13 |
| Q16663 | C-C motif chemokine 15 |
| Q92583 | C-C motif chemokine 17 |
| Q99731 | C-C motif chemokine 19 |
| P78556 | C-C motif chemokine 20 |
| O00585 | C-C motif chemokine 21 |
| O00626 | C-C motif chemokine 22 |
| P55773 | C-C motif chemokine 23 |
| O00175 | C-C motif chemokine 24 |
| Q9Y258 | C-C motif chemokine 26 |
| Q9Y4X3 | C-C motif chemokine 27 |
| P10147 | C-C motif chemokine 3 |
| P13236 | C-C motif chemokine 4 |
| P80098 | C-C motif chemokine 7 |
| P80075 | C-C motif chemokine 8 |
| P00450 | Ceruloplasmin |
| P01233 | Choriogonadotropin subunit beta |
| P45452 | Collagenase 3 |
| P01308 (aa57-87) | C-Peptide |
| P12277; P06732 | Creatine Kinase-MB |
| P02778 | C-X-C motif chemokine 10 |
| O14625 | C-X-C motif chemokine 11 |
| O43927 | C-X-C motif chemokine 13 |
| Q9H2A7 | C-X-C motif chemokine 16 |
| P42830 | C-X-C motif chemokine 5 |
| P80162 | C-X-C motif chemokine 6 |
| Q07325 | C-X-C motif chemokine 9 |
| P01034 | Cystatin-C |
| Q9UNN8 | Endothelial protein C receptor |
| P51671 | Eotaxin |
| P00533 | Epidermal growth factor receptor |
| P02792; P02794 | Ferritin |
| P02671; P02675; P02679 | Fibrinogen |
| P09681 | Gastric inhibitory polypeptide |
| P01275 | Glucagon |
| P01275 (aa98-127; aa98-128) | Glucagon-like peptide 1 |
| P04141 | Granulocyte-macrophage colony-stimulating factor |
| P09341; P19875; P19876 | Growth-regulated alpha, beta, and gamma proteins |
| P09038 | Heparin-binding growth factor 2 |
| P14210 | Hepatocyte growth factor |
| N/A | Immunoglobulin A |
| n/a | Immunoglobulin M |
| n/a | Immunoglulin G1 |
| N/A | Immunoglulin G2 |
| N/A | Immunoglulin G3 |
| n/a | Immunoglulin G4 |
| P01308 | Insulin |
| P08833 | Insulin-like growth factor-binding protein 1 |
| P18065 | Insulin-like growth factor-binding protein 2 |
| P17936 | Insulin-like growth factor-binding protein 3 |
| P22692 | Insulin-like growth factor-binding protein 4 |
| P24593 | Insulin-like growth factor-binding protein 5 |
| P24592 | Insulin-like growth factor-binding protein 6 |
| Q16270 | Insulin-like growth factor-binding protein 7 |
| P01563 | Interferon alpha-2 |
| P01579 | Interferon gamma |
| P01583 | Interleukin-1 alpha |
| P01584 | Interleukin-1 beta |
| P18510 | Interleukin-1 receptor antagonist protein |
| P14778 | Interleukin-1 receptor type I |
| P27930 | Interleukin-1 receptor type II |
| P20809 | Interleukin-11 |
| P29459; P29460 | Interleukin-12 |
| P29460 | Interleukin-12 subunit beta |
| P35225 | Interleukin-13 |
| P40933 | Interleukin-15 |
| P60568 | Interleukin-2 |
| Q9NYY1 | Interleukin-20 |
| Q9HBE4 | Interleukin-21 |
| Q9NPF7; P29460 | Interleukin-23 |
| Q8IZJ0 | Interleukin-28A |
| Q8IU54 | Interleukin-29 |
| P08700 | Interleukin-3 |
| O95760 | Interleukin-33 |
| P05112 | Interleukin-4 |
| P05113 | Interleukin-5 |
| P08887 | Interleukin-6 receptor subunit alpha |
| P40189 | Interleukin-6 receptor subunit beta |
| P13232 | Interleukin-7 |
| P15248 | Interleukin-9 |
| P03956 | Interstitial collagenase |
| P10997 | Islet amyloid polypeptide |
| P08727 | Keratin, type I cytoskeletal 19 (aa311-367) |
| P21583 | Kit ligand |
| P41159 | Leptin |
| P15018 | Leukemia inhibitory factor |
| P47992 | Lymphotactin |
| P01374 | Lymphotoxin-alpha |
| P09603 | Macrophage colony-stimulating factor 1 |
| P39900 | Macrophage metalloelastase |
| P14174 | Macrophage migration inhibitory factor |
| P09237 | Matrilysin |
| P01033 | Metalloproteinase inhibitor 1 |
| P16035 | Metalloproteinase inhibitor 2 |
| P35625 | Metalloproteinase inhibitor 3 |
| Q99727 | Metalloproteinase inhibitor 4 |
| P02144 | Myoglobin |

-continued

| SwissProtNum | Preferred Name |
| --- | --- |
| P01298 | Pancreatic prohormone |
| P10082 | Peptide YY |
| P01133 | Pro-epidermal growth factor |
| Q14005 | Pro-interleukin-16 |
| P01236 | Prolactin |
| P07288 | Prostate-specific antigen |
| P80511 | Protein S100-A12 |
| P01135 | Protransforming growth factor alpha |
| N/A | Secretory immunoglobulin A |
| P02743 | Serum amyloid P-component |
| P49771 | SL cytokine |
| P48061 | Stromal cell-derived factor 1 |
| P08254 | Stromelysin-1 |
| P40225 | Thrombopoietin |
| Q969D9 | Thymic stromal lymphopoietin |
| P01375 | Tumor necrosis factor |
| P50591 | Tumor necrosis factor ligand superfamily member 10 |
| P48023 | Tumor necrosis factor ligand superfamily member 6 |
| P19438 | Tumor necrosis factor receptor superfamily member 1A |
| P20333 | Tumor necrosis factor receptor superfamily member 1B |
| P17948 | Vascular endothelial growth factor receptor 1 |
| P35968 | Vascular endothelial growth factor receptor 2 |
| P35916 | Vascular endothelial growth factor receptor 3 |
| P04275 | von Willebrand Factor |
| Q14508 | WAP four-disulfide core domain protein 2 |
| P05231 | Interleukin-6 |
| P08253 | 72 kDa type IV collagenase |

Marker Assays

In general, immunoassays involve contacting a sample containing or suspected of containing a biomarker of interest with at least one antibody that specifically binds to the biomarker. A signal is then generated indicative of the presence or amount of complexes formed by the binding of polypeptides in the sample to the antibody. The signal is then related to the presence or amount of the biomarker in the sample. Numerous methods and devices are well known to the skilled artisan for the detection and analysis of biomarkers. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and The Immunoassay Handbook, David Wild, ed. Stockton Press, New York, 1994, each of which is hereby incorporated by reference in its entirety, including all tables, figures and claims.

The assay devices and methods known in the art can utilize labeled molecules in various sandwich, competitive, or non-competitive assay formats, to generate a signal that is related to the presence or amount of the biomarker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing immunoassays. But any suitable immunoassay may be utilized, for example, enzyme-linked immunoassays (ELISA), radioimmunoassays (RIAs), competitive binding assays, and the like.

Antibodies or other polypeptides may be immobilized onto a variety of solid supports for use in assays. Solid phases that may be used to immobilize specific binding members include include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

Biological assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

In certain aspects, the present invention provides kits for the analysis of the described appendicitis biomarkers. The kit comprises reagents for the analysis of at least one test sample which comprise at least one antibody that binds an appendicitis biomarker. The kit can also include devices and instructions for performing one or more of the diagnostic and/or prognostic correlations described herein. Preferred kits will comprise an antibody pair for performing a sandwich assay, or a labeled species for performing a competitive assay, for the analyte. Preferably, an antibody pair comprises a first antibody conjugated to a solid phase and a second antibody conjugated to a detectable label, wherein each of the first and second antibodies bind an appendicitis biomarker. Most preferably each of the antibodies are monoclonal antibodies. The instructions for use of the kit and performing the correlations can be in the form of labeling, which refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

Antibodies

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Antibodies used in the immunoassays described herein preferably specifically bind to an appendicitis biomarker of the present invention. The term "specifically binds" is not intended to indicate that an antibody binds exclusively to its intended target since, as noted above, an antibody binds to any polypeptide displaying the epitope(s) to which the antibody binds. Rather, an antibody "specifically binds" if its affinity for its intended target is about 5-fold greater when compared to its affinity for a non-target molecule which does not display the appropriate epitope(s). Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, preferred antibodies bind with affinities of at least about $10^7$ $M^{-1}$, and preferably between about $10^8$ $M^{-1}$ to about $10^9$ $M^{-1}$, about $10^9$ $M^{-1}$ to about $10^{10}$ $M^{-1}$, or about $10^{10}$ $M^{-1}$ to about $10^{12}$ $M^{-1}$.

Affinity is calculated as $K_d=k_{off}/k_{on}$ ($k_{off}$ is the dissociation rate constant, $K_{on}$ is the association rate constant and $K_d$ is the equilibrium constant). Affinity can be determined at equilibrium by measuring the fraction bound (r) of labeled ligand at various concentrations (c). The data are graphed using the Scatchard equation: $r/c=K(n-r)$: where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

The term "epitope" refers to an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Numerous publications discuss the use of phage display technology to produce and screen libraries of polypeptides for binding to a selected analyte. See, e.g., Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

While the present application describes antibody-based binding assays in detail, alternatives to antibodies as binding species in assays are well known in the art. These include receptors for a particular target, aptamers, etc. Aptamers are oligonucleic acid or peptide molecules that bind to a specific target molecule. Aptamers are usually created by selecting them from a large random sequence pool, but natural aptamers also exist. High-affinity aptamers containing modified nucleotides can confer improved characteristics on the ligand, such as improved in vivo stability or improved delivery characteristics. Examples of such modifications include chemical substitutions at the ribose and/or phosphate and/or base positions, and may include amino acid side chain functionalities.

Assay Correlations

The term "correlating" as used herein in reference to the use of biomarkers refers to comparing the presence or amount of the biomarker(s) in a patient to its presence or amount in persons known to suffer from, or known to be at risk of, a given condition; or in persons known to be free of a given condition. Often, this takes the form of comparing an assay result in the form of a biomarker concentration to a predetermined threshold selected to be indicative of the occurrence or nonoccurrence of a disease or the likelihood of some future outcome.

Selecting a diagnostic threshold involves, among other things, consideration of the probability of disease, distribution of true and false diagnoses at different test thresholds, and estimates of the consequences of treatment (or a failure to treat) based on the diagnosis. For example, when considering administering a specific therapy which is highly efficacious and has a low level of risk, few tests are needed because clinicians can accept substantial diagnostic uncertainty. On the other hand, in situations where treatment options are less effective and more risky, clinicians often need a higher degree of diagnostic certainty. Thus, cost/benefit analysis is involved in selecting a diagnostic threshold.

Suitable thresholds may be determined in a variety of ways. For example, one recommended diagnostic threshold for the diagnosis of acute myocardial infarction using cardiac troponin is the 97.5th percentile of the concentration seen in a normal population. Another method may be to look at serial samples from the same patient, where a prior "baseline" result is used to monitor for temporal changes in a biomarker level.

Population studies may also be used to select a decision threshold. Receiver Operating Characteristic ("ROC") arose from the field of signal detection theory developed during World War II for the analysis of radar images, and ROC analysis is often used to select a threshold able to best distinguish a "diseased" subpopulation from a "nondiseased" subpopulation. A false positive in this case occurs when the person tests positive, but actually does not have the disease. A false negative, on the other hand, occurs when the person tests negative, suggesting they are healthy, when they actually do have the disease. To draw a ROC curve, the true positive rate (TPR) and false positive rate (FPR) are determined as the decision threshold is varied continuously. Since TPR is equivalent with sensitivity and FPR is equal to 1−specificity, the ROC graph is sometimes called the sensitivity vs (1−specificity) plot. A perfect test will have an area under the ROC curve of 1.0; a random test will have an area of 0.5. A threshold is selected to provide an acceptable level of specificity and sensitivity.

In this context, "diseased" is meant to refer to a population having one characteristic (the presence of a disease or condition or the occurrence of some outcome) and "nondiseased" is meant to refer to a population lacking the characteristic. While a single decision threshold is the simplest application of such a method, multiple decision thresholds may be used. For example, below a first threshold, the absence of disease may be assigned with relatively high confidence, and above a second threshold the presence of disease may also be assigned with relatively high confidence. Between the two thresholds may be considered indeterminate. This is meant to be exemplary in nature only.

In addition to threshold comparisons, other methods for correlating assay results to a patient classification (occurrence or nonoccurrence of disease, likelihood of an outcome, etc.) include decision trees, rule sets, Bayesian methods, and neural network methods. These methods can produce probability values representing the degree to which a patient belongs to one classification out of a plurality of classifications.

Measures of test accuracy may be obtained as described in Fischer et al., *Intensive Care Med.* 29: 1043-51, 2003, and used to determine the effectiveness of a given biomarker. These measures include sensitivity and specificity, predictive values, likelihood ratios, diagnostic odds ratios, and ROC curve areas. The area under the curve ("AUC") of a ROC plot is equal to the probability that a classifier will rank a randomly chosen positive instance higher than a randomly chosen negative one. The area under the ROC curve may be thought of as equivalent to the Mann-Whitney U test, which tests for the median difference between scores obtained in the two groups considered if the groups are of continuous data, or to the Wilcoxon test of ranks.

As discussed above, suitable tests may exhibit one or more of the following results on these various measures: a specificity of greater than 0.5, preferably at least 0.6, more preferably at least 0.7, still more preferably at least 0.8, even more preferably at least 0.9 and most preferably at least 0.95, with a corresponding sensitivity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; a sensitivity of greater than 0.5, preferably at least 0.6, more preferably at least 0.7, still more preferably at least 0.8, even more preferably at least 0.9 and most preferably at least 0.95, with a corresponding specificity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; at least 75% sensitivity, combined with at least 75% specificity; a ROC curve area of greater than 0.5, preferably at least 0.6, more preferably 0.7, still more preferably at least 0.8, even more preferably at least 0.9, and most preferably at least 0.95; an odds ratio different from 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less; a positive likelihood ratio (calculated as sensitivity/(1−specificity)) of greater than 1, at least 2, more preferably at least 3, still more preferably at least 5, and most preferably at least 10; and or a negative likelihood ratio (calculated as (1-sensitivity)/specificity) of less than 1, less than or equal to 0.5, more preferably less than or equal to 0.3, and most preferably less than or equal to 0.1

Additional clinical indicia may be combined with the appendicitis biomarker assay result(s) of the present invention. Other clinical indicia which may be combined with the appendicitis biomarker assay result(s) of the present invention includes demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, or renal insufficiency), risk scores (APACHE score, PREDICT score, TIMI Risk Score for UA/NSTEMI, Framingham Risk Score), etc.

Combining assay results/clinical indicia in this manner can comprise the use of multivariate logistical regression, loglinear modeling, neural network analysis, n-of-m analysis, decision tree analysis, etc. This list is not meant to be limiting.

Selecting a Treatment Regimen

Once a diagnosis is obtained, the clinician can readily select a treatment regimen that is compatible with the diagnosis. The skilled artisan is aware of appropriate treatments for numerous diseases discussed in relation to the methods of diagnosis described herein. See, e.g., Merck Manual of Diagnosis and Therapy, 17th Ed. Merck Research Laboratories, Whitehouse Station, N J, 1999. In addition, since the methods and compositions described herein provide prognostic information, the markers of the present invention may be used to monitor a course of treatment. For example, improved or worsened prognostic state may indicate that a particular treatment is or is not efficacious.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

Example 1

Immunoassay Format

Analytes are measured using standard sandwich enzyme immunoassay techniques. A first antibody which binds the analyte is immobilized in wells of a 96 well polystyrene microplate. Analyte standards and test samples are pipetted into the appropriate wells and any analyte present is bound by the immobilized antibody. After washing away any unbound substances, a horseradish peroxidase-conjugated second antibody which binds the analyte is added to the wells, thereby forming sandwich complexes with the analyte (if present) and the first antibody. Following a wash to remove any unbound antibody-enzyme reagent, a substrate solution comprising tetramethylbenzidine and hydrogen peroxide is added to the wells. Color develops in proportion to the amount of analyte present in the sample. The color development is stopped and the intensity of the color is measured at 540 nm or 570 nm. An analyte concentration is assigned to the test sample by comparison to a standard curve determined from the analyte standards.

Example 2

Use of Analyte as a Marker for Assessing Patients for Appendicitis

Patients from the emergency department (ED) classified as positive for appendicitis according to clinical diagnosis at the study site were selected as a "diseased" cohort ("Cohort 1"). Plasma and urine samples from each patient in Cohort 1 were collected at the time of appendectomy. Cohort 2 was a normal population sampled separately. The concentrations of the analyte in these samples were measured by standard immunoassay methods using commercially available assay reagents. A receiver operating characteristic (ROC) curve was generated using the concentrations, and the performance of the analyte is assessed by the area under the ROC curve (AUC). The two-tailed p-value of the AUC for the analyte was also calculated to determine statistical significance. "Inc/Dec" indicates if the marker is increasing or decreasing in Cohort 1 relative to Cohort 2.

TABLE 1

Urine samples

| Preferred Name | Units | Increasing/Decreasing | p |
| --- | --- | --- | --- |
| Adiponectin | ng/ml | inc | 8.68E−07 |
| Advanced glycosylation end product-specific receptor | pg/ml | dec | 2.82E−01 |
| Alpha-2 macroglobulin | ug/ml | inc | 1.51E−04 |
| Alpha-2-HS-glycoprotein | ng/ml | inc | 1.97E−02 |
| Angiopoietin-1 | ng/ml | dec | 7.54E−01 |
| Antileukoproteinase | pg/ml | dec | 9.51E−01 |
| Apolipoprotein(a) | ng/ml | dec | 6.85E−05 |
| Carbonic anhydrase 9 | ng/ml | inc | 3.80E−01 |
| C-C motif chemokine 1 | pg/ml | inc | 7.88E−01 |
| C-C motif chemokine 13 | pg/ml | dec | 3.19E−01 |
| C-C motif chemokine 15 | pg/ml | dec | 1.45E−01 |
| C-C motif chemokine 17 | pg/ml | inc | 6.55E−01 |
| C-C motif chemokine 19 | pg/ml | dec | 5.62E−02 |
| C-C motif chemokine 20 | pg/ml | dec | 2.49E−01 |
| C-C motif chemokine 21 | pg/ml | inc | 7.47E−01 |
| C-C motif chemokine 22 | pg/ml | inc | 7.81E−01 |
| C-C motif chemokine 23 | ng/ml | inc | 5.63E−01 |
| C-C motif chemokine 24 | pg/ml | inc | 3.00E−02 |
| C-C motif chemokine 26 | pg/ml | dec | 6.44E−01 |
| C-C motif chemokine 27 | pg/ml | inc | 3.18E−01 |
| C-C motif chemokine 3 | pg/ml | dec | 3.36E−01 |
| C-C motif chemokine 4 | pg/ml | inc | 6.33E−01 |
| C-C motif chemokine 7 | pg/ml | inc | 6.44E−01 |
| C-C motif chemokine 8 | pg/ml | inc | 8.29E−01 |
| Ceruloplasmin | ng/ml | dec | 8.02E−02 |
| C-Peptide | pg/ml | dec | 3.35E−04 |
| Creatine Kinase-MB | ng/ml | inc | 7.18E−01 |
| C-X-C motif chemokine 10 | pg/ml | inc | 6.59E−02 |
| C-X-C motif chemokine 11 | pg/ml | inc | 6.35E−01 |
| C-X-C motif chemokine 13 | pg/ml | dec | 6.57E−01 |
| C-X-C motif chemokine 16 | ng/ml | inc | 4.61E−01 |
| C-X-C motif chemokine 5 | pg/ml | inc | 8.20E−01 |
| C-X-C motif chemokine 6 | pg/ml | inc | 8.93E−06 |
| C-X-C motif chemokine 9 | pg/ml | inc | 2.25E−01 |
| Cystatin-C | ng/ml | dec | 2.01E−01 |
| Endothelial protein C receptor | ng/ml | inc | 1.26E−02 |
| Eotaxin | pg/ml | inc | 7.99E−01 |
| Epidermal growth factor receptor | pg/ml | inc | 7.11E−01 |
| Ferritin | pg/ml | inc | 5.59E−06 |
| Fibrinogen | ng/ml | inc | 7.56E−01 |
| Gastric inhibitory polypeptide | pg/ml | inc | 6.44E−01 |
| Glucagon | pg/ml | dec | 8.18E−01 |
| Glucagon-like peptide 1 | pg/ml | inc | 8.18E−01 |
| Granulocyte-macrophage colony-stimulating factor | pg/ml | dec | 9.87E−02 |
| Heparin-binding growth factor 2 | pg/ml | dec | 7.31E−01 |
| Hepatocyte growth factor | ng/ml | dec | 6.68E−01 |
| Immunoglobulin A | ng/ml | inc | 6.83E−01 |
| Immunoglobulin M | ng/ml | inc | 2.64E−08 |
| Immuniglogulin G1 | ng/ml | dec | 1.37E−02 |
| Immuniglogulin G2 | ng/ml | dec | 2.19E−01 |
| Immuniglogulin G3 | ng/ml | dec | 7.25E−01 |
| Immuniglogulin G4 | ng/ml | inc | 4.56E−03 |
| Insulin | pg/ml | dec | 4.31E−02 |
| Insulin-like growth factor-binding protein 1 | ng/ml | dec | 2.00E−03 |
| Insulin-like growth factor-binding protein 2 | ng/ml | dec | 0.00E+00 |
| Insulin-like growth factor-binding protein 3 | ng/ml | dec | 1.96E−01 |
| Insulin-like growth factor-binding protein 4 | ng/ml | inc | 8.52E−01 |
| Insulin-like growth factor-binding protein 5 | ng/ml | dec | 6.96E−01 |
| Insulin-like growth factor-binding protein 6 | ng/ml | inc | 1.17E−01 |
| Insulin-like growth factor- | ng/ml | inc | 2.36E−01 |

TABLE 1-continued

Urine samples

| Preferred Name | Units | Increasing/Decreasing | p |
|---|---|---|---|
| binding protein 7 | | | |
| Interferon alpha-2 | pg/ml | dec | 2.86E−01 |
| Interferon gamma | pg/ml | inc | 8.31E−01 |
| Interleukin-1 alpha | pg/ml | dec | 5.10E−01 |
| Interleukin-1 beta | pg/ml | dec | 9.67E−01 |
| Interleukin-1 receptor antagonist protein | pg/ml | dec | 4.62E−02 |
| Interleukin-1 receptor type I | pg/mL | inc | 3.16E−01 |
| Interleukin-1 receptor type II | pg/mL | inc | 9.27E−01 |
| Interleukin-11 | pg/ml | dec | 7.53E−03 |
| Interleukin-12 | pg/ml | inc | 8.48E−01 |
| Interleukin-12 subunit beta | ng/ml | dec | 5.34E−02 |
| Interleukin-13 | pg/ml | dec | 8.78E−01 |
| Interleukin-15 | pg/ml | dec | 2.31E−01 |
| Interleukin-2 | pg/ml | dec | 5.87E−01 |
| Interleukin-20 | pg/ml | dec | 3.22E−01 |
| Interleukin-21 | pg/ml | dec | 4.17E−01 |
| Interleukin-23 | pg/ml | inc | 6.19E−01 |
| Interleukin-28A | pg/ml | inc | 4.52E−01 |
| Interleukin-29 | pg/ml | inc | 3.74E−02 |
| Interleukin-3 | pg/ml | inc | 3.48E−01 |
| Interleukin-33 | pg/ml | inc | 2.14E−01 |
| Interleukin-4 | pg/ml | inc | 5.71E−01 |
| Interleukin-5 | ng/ml | inc | 8.08E−01 |
| Interleukin-6 receptor subunit alpha | pg/ml | inc | 6.70E−01 |
| Interleukin-6 receptor subunit beta | pg/ml | dec | 6.63E−01 |
| Interleukin-7 | pg/ml | dec | 8.59E−01 |
| Interleukin-9 | pg/ml | inc | 4.32E−01 |
| Islet amyloid polypeptide | pg/ml | dec | 8.78E−01 |
| Kit ligand | pg/ml | dec | 3.64E−01 |
| Leptin | pg/ml | dec | 3.21E−01 |
| Leukemia inhibitory factor | pg/ml | dec | 8.27E−01 |
| Lymphotactin | pg/ml | inc | 4.48E−01 |
| Lymphotoxin-alpha | pg/ml | dec | 6.44E−01 |
| Macrophage colony-stimulating factor 1 | pg/ml | inc | 1.01E−01 |
| Metalloproteinase inhibitor 1 | pg/ml | inc | 7.52E−01 |
| Metalloproteinase inhibitor 2 | pg/ml | inc | 1.78E−01 |
| Metalloproteinase inhibitor 3 | pg/ml | inc | 8.45E−01 |
| Metalloproteinase inhibitor 4 | pg/ml | dec | 1.62E−01 |
| Mix of Growth-regulated alpha, beta, and gamma proteins | pg/ml | inc | 4.65E−01 |
| Myoglobin | ng/ml | dec | 1.14E−02 |
| Pancreatic prohormone | pg/ml | dec | 5.89E−01 |
| Peptide YY | pg/ml | dec | 8.18E−01 |
| Pro-epidermal growth factor | pg/ml | inc | 5.02E−02 |
| Pro-interleukin-16 | pg/ml | dec | 9.39E−01 |
| Protein S100-A12 | ng/ml | dec | 2.49E−02 |
| Protransforming growth factor alpha | pg/ml | inc | 5.62E−02 |
| Secretory immunoglobulin A | ng/ml | inc | 9.18E−01 |
| Serum amyloid P-component | ng/ml | inc | 1.02E−04 |
| SL cytokine | pg/ml | dec | 7.11E−01 |
| Stromal cell-derived factor 1 | pg/ml | dec | 7.03E−02 |
| Thrombopoietin | pg/ml | dec | 1.15E−02 |
| Thymic stromal lymphopoietin | pg/ml | inc | 1.81E−03 |
| Tumor necrosis factor | pg/ml | dec | 8.29E−01 |
| Tumor necrosis factor ligand superfamily member 10 | pg/ml | inc | 1.24E−01 |
| Tumor necrosis factor receptor superfamily member 1A | pg/ml | dec | 5.55E−03 |
| Tumor necrosis factor receptor superfamily member 1B | pg/ml | dec | 4.11E−02 |
| Vascular endothelial growth factor receptor 1 | pg/ml | dec | 1.11E−01 |
| Vascular endothelial growth factor receptor 2 | pg/ml | dec | 6.61E−01 |
| Vascular endothelial growth factor receptor 3 | pg/ml | dec | 9.11E−01 |
| von Willebrand Factor | ng/ml | inc | 2.52E−04 |

TABLE 2

Plasma samples

| Preferred Name | Units | Increasing/Decreasing | p |
|---|---|---|---|
| 72 kDa type IV collagenase | pg/ml | inc | 1.73E−14 |
| Adiponectin | ng/ml | inc | 8.92E−01 |
| Advanced glycosylation end product-specific receptor | pg/ml | inc | 3.24E−01 |
| Alpha-2 macroglobulin | ug/ml | dec | 1.52E−01 |
| Alpha-2-HS-glycoprotein | ng/ml | inc | 4.26E−04 |
| Alpha-fetoprotein | pg/ml | inc | 8.85E−01 |
| Angiopoietin-1 | ng/ml | inc | 1.75E−02 |
| Antileukoproteinase | pg/ml | dec | 3.89E−01 |
| Apolipoprotein(a) | ng/ml | inc | 3.51E−01 |
| Cancer Antigen 15-3 | U/ml | inc | 9.18E−06 |
| Cancer Antigen 19-9 | U/ml | inc | 6.13E−01 |
| Carbonic anhydrase 9 | ng/ml | inc | 3.78E−02 |
| Carcinoembryonic antigen-related cell adhesion molecule 5 | pg/ml | dec | 9.44E−01 |
| C-C motif chemokine 1 | pg/ml | dec | 1.79E−01 |
| C-C motif chemokine 13 | pg/ml | inc | 5.89E−03 |
| C-C motif chemokine 15 | pg/ml | dec | 1.67E−01 |
| C-C motif chemokine 17 | pg/ml | inc | 1.69E−01 |
| C-C motif chemokine 19 | pg/ml | inc | 2.24E−03 |
| C-C motif chemokine 20 | pg/ml | dec | 4.43E−01 |
| C-C motif chemokine 21 | pg/ml | dec | 1.43E−02 |
| C-C motif chemokine 22 | pg/ml | dec | 3.28E−06 |
| C-C motif chemokine 23 | ng/ml | inc | 1.25E−08 |
| C-C motif chemokine 24 | pg/ml | inc | 3.32E−01 |
| C-C motif chemokine 26 | pg/ml | inc | 1.54E−01 |
| C-C motif chemokine 27 | pg/ml | dec | 1.44E−02 |
| C-C motif chemokine 3 | pg/ml | dec | 1.81E−01 |
| C-C motif chemokine 4 | pg/ml | inc | 3.44E−04 |
| C-C motif chemokine 7 | pg/ml | inc | 8.34E−01 |
| C-C motif chemokine 8 | pg/ml | dec | 9.23E−01 |
| Ceruloplasmin | ng/ml | dec | 9.62E−02 |
| Choriogonadotropin subunit beta | mU/ml | inc | 2.52E−02 |
| Collagenase 3 | pg/ml | dec | 4.64E−01 |
| C-Peptide | pg/ml | dec | 2.52E−05 |
| Creatine Kinase-MB | ng/ml | inc | 3.37E−01 |
| C-X-C motif chemokine 10 | pg/ml | inc | 1.08E−01 |
| C-X-C motif chemokine 11 | pg/ml | dec | 6.95E−02 |
| C-X-C motif chemokine 13 | pg/ml | dec | 5.59E−03 |
| C-X-C motif chemokine 16 | ng/ml | dec | 1.47E−02 |
| C-X-C motif chemokine 5 | pg/ml | dec | 9.76E−01 |
| C-X-C motif chemokine 6 | pg/ml | inc | 1.04E−01 |
| C-X-C motif chemokine 9 | pg/ml | inc | 4.93E−01 |
| Cystatin-C | ng/ml | inc | 8.02E−07 |
| Endothelial protein C receptor | ng/ml | dec | 3.19E−01 |
| Eotaxin | pg/ml | inc | 1.20E−07 |
| Epidermal growth factor receptor | pg/ml | dec | 6.80E−01 |
| Ferritin | pg/ml | dec | 1.92E−04 |
| Fibrinogen | ug/ml | dec | 5.85E−02 |
| Gastric inhibitory polypeptide | pg/ml | dec | 0.00E+00 |
| Glucagon | pg/ml | dec | 8.82E−01 |
| Glucagon-like peptide 1 | pg/ml | dec | 6.75E−04 |
| Granulocyte-macrophage colony-stimulating factor | pg/ml | inc | 2.07E−02 |
| Heparin-binding growth factor 2 | pg/ml | inc | 7.22E−01 |
| Hepatocyte growth factor | ng/ml | inc | 0.00E+00 |
| Immunoglobulin A | ng/ml | dec | 4.10E−03 |
| Immunoglobulin M | ng/ml | dec | 5.79E−01 |
| Immunoglogulin G1 | ng/ml | dec | 4.93E−01 |
| Immunoglogulin G2 | ng/ml | dec | 3.03E−01 |
| Immunoglogulin G3 | ng/ml | dec | 2.08E−04 |
| Immunoglogulin G4 | ng/ml | dec | 4.64E−01 |
| Insulin | pg/ml | dec | 8.32E−05 |
| Insulin-like growth factor-binding protein 1 | ng/ml | dec | 2.19E−10 |
| Insulin-like growth factor-binding protein 2 | ng/ml | dec | 8.69E−01 |
| Insulin-like growth factor-binding protein 3 | ng/ml | inc | 1.75E−01 |
| Insulin-like growth factor-binding protein 4 | ng/ml | dec | 5.07E−01 |
| Insulin-like growth factor-binding protein 5 | ng/ml | dec | 9.25E−04 |
| Insulin-like growth factor-binding protein 6 | ng/ml | inc | 1.68E−07 |

TABLE 2-continued

Plasma samples

| Preferred Name | Units | Increasing/Decreasing | p |
|---|---|---|---|
| Insulin-like growth factor-binding protein 7 | ng/ml | dec | 7.07E−05 |
| Interferon alpha-2 | pg/ml | inc | 1.55E−01 |
| Interferon gamma | pg/ml | inc | 1.04E−02 |
| Interleukin-1 alpha | pg/ml | dec | 8.53E−01 |
| Interleukin-1 beta | pg/ml | dec | 1.45E−01 |
| Interleukin-1 receptor type I | pg/mL | dec | 1.60E−03 |
| Interleukin-1 receptor type II | pg/mL | inc | 7.29E−01 |
| Interleukin-11 | pg/ml | inc | 5.15E−01 |
| Interleukin-12 | pg/ml | inc | 5.94E−01 |
| Interleukin-12 subunit beta | ng/ml | dec | 9.09E−01 |
| Interleukin-13 | pg/ml | inc | 4.61E−01 |
| Interleukin-15 | pg/ml | dec | 7.13E−02 |
| Interleukin-2 | pg/ml | dec | 1.90E−03 |
| Interleukin-20 | pg/ml | inc | 5.51E−01 |
| Interleukin-21 | pg/ml | dec | 9.01E−01 |
| Interleukin-23 | pg/ml | dec | 5.67E−01 |
| Interleukin-28A | pg/ml | dec | 4.44E−01 |
| Interleukin-29 | pg/ml | dec | 3.04E−01 |
| Interleukin-3 | pg/ml | inc | 6.55E−01 |
| Interleukin-33 | pg/ml | dec | 5.24E−01 |
| Interleukin-4 | pg/ml | dec | 4.79E−01 |
| Interleukin-5 | ng/ml | inc | 2.65E−01 |
| Interleukin-6 receptor subunit alpha | pg/ml | dec | 2.88E−01 |
| Interleukin-6 receptor subunit beta | pg/ml | dec | 5.47E−01 |
| Interleukin-7 | pg/ml | inc | 7.57E−01 |
| Interleukin-9 | pg/ml | dec | 5.16E−01 |
| Interstitial collagenase | pg/ml | dec | 1.78E−01 |
| Islet amyloid polypeptide | pg/ml | inc | 2.96E−07 |
| Keratin, type I cytoskeletal 19 (aa311-367) | pg/ml | dec | 9.39E−01 |
| Kit ligand | pg/ml | inc | 8.87E−01 |
| Leptin | pg/ml | dec | 8.44E−01 |
| Leukemia inhibitory factor | pg/ml | dec | 3.49E−01 |
| Lymphotactin | pg/ml | dec | 5.21E−02 |
| Lymphotoxin-alpha | pg/ml | inc | 6.48E−01 |
| Macrophage colony-stimulating factor 1 | pg/ml | dec | 7.41E−04 |
| Macrophage metalloelastase | pg/ml | inc | 8.74E−01 |
| Macrophage migration inhibitory factor | pg/ml | inc | 5.75E−06 |
| Matrilysin | pg/ml | dec | 1.59E−01 |
| Metalloproteinase inhibitor 1 | pg/ml | dec | 9.56E−01 |
| Metalloproteinase inhibitor 2 | pg/ml | inc | 4.10E−09 |
| Metalloproteinase inhibitor 3 | pg/ml | inc | 2.28E−01 |
| Metalloproteinase inhibitor 4 | pg/ml | inc | 4.21E−01 |
| Mix of Growth-regulated alpha, beta, and gamma proteins | pg/ml | inc | 2.33E−01 |
| Myoglobin | ng/ml | dec | 5.72E−01 |
| Pancreatic prohormone | pg/ml | inc | 2.44E−13 |
| Peptide YY | pg/ml | inc | 1.32E−03 |
| Pro-epidermal growth factor | pg/ml | inc | 1.23E−02 |
| Pro-interleukin-16 | pg/ml | inc | 3.21E−01 |
| Prolactin | pg/ml | dec | 2.55E−11 |
| Prostate-specific antigen | pg/ml | dec | 7.49E−01 |
| Protein S100-A12 | ng/ml | dec | 2.02E−04 |
| Protransforming growth factor alpha | pg/ml | inc | 3.50E−02 |
| Serum amyloid P-component | ng/ml | dec | 4.77E−01 |
| SL cytokine | pg/ml | dec | 1.27E−01 |
| Stromal cell-derived factor 1 | pg/ml | inc | 8.60E−01 |
| Stromelysin-1 | pg/ml | dec | 2.76E−06 |
| Thrombopoietin | pg/ml | inc | 1.76E−04 |
| Thymic stromal lymphopoietin | pg/ml | dec | 5.75E−01 |
| Tumor necrosis factor | pg/ml | dec | 1.15E−01 |
| Tumor necrosis factor ligand superfamily member 10 | pg/ml | inc | 1.03E−06 |
| Tumor necrosis factor ligand superfamily member 6 | pg/ml | dec | 3.96E−01 |
| Tumor necrosis factor receptor superfamily member 1A | pg/ml | dec | 1.20E−07 |
| Tumor necrosis factor receptor superfamily member 1B | pg/ml | dec | 1.03E−02 |
| Vascular endothelial growth factor receptor 1 | pg/ml | inc | 6.04E−07 |
| Vascular endothelial growth factor receptor 2 | pg/ml | dec | 2.63E−03 |
| Vascular endothelial growth factor receptor 3 | pg/ml | inc | 8.51E−01 |
| von Willebrand Factor | ng/ml | dec | 8.01E−01 |
| WAP four-disulfide core domain protein 2 | pg/ml | dec | 4.13E−04 |

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method of detecting C-C motif chemokine 4 in a subject who is being evaluated for appendicitis, the method comprising:
   a) performing an assay configured to detect C-C motif chemokine 4 on a body fluid sample obtained from the subject who is being evaluated for appendicitis to provide an assay result,
   b) diagnosing the subject with appendicitis based on the assay result, and c) treating the subject diagnosed with appendicitis by appendectomy.

2. The method according to claim 1, wherein the performing step comprises introducing the body fluid sample obtained from the subject into an assay instrument, wherein the assay instrument (i) contacts the body fluid sample with a binding reagent specific for C-C motif chemokine 4, wherein C-C motif chemokine 4 binds to the binding reagent in an amount related to concentration in the body fluid sample, (ii) generates an assay result indicative of binding of C-C motif chemokine 4 to the binding reagent; and (iii) displays the assay result as a quantitative result in a human-readable form.

3. The method according to claim 1, wherein the subject has abdominal pain.

4. The method according to claim 1, wherein the body fluid sample is selected from the group consisting of urine, blood, serum, and plasma.

5. The method of claim 1, wherein the assay result is a measured concentration of C-C motif chemokine 4.

6. The method of claim 1, wherein the assay is an immunoassay.

7. The method of claim 2, wherein the assay is an immunoassay.

8. The method of claim 7, wherein the assay is a sandwich immunoassay.

9. The method of claim 4, wherein the body fluid sample is plasma.

10. The method of claim 4, wherein the body fluid sample is urine.

11. A method for evaluating biomarker levels in a body fluid sample comprising:
    obtaining the body fluid sample from a subject who is being evaluated for appendicitis;
    performing an analyte binding assay configured to detect C-C motif chemokine 4 by introducing the body fluid sample obtained from the subject into an assay instrument, wherein the assay instrument (i) contacts the body fluid sample with a binding reagent specific for C-C motif chemokine 4, wherein C-C motif chemokine 4 binds to the binding reagent in an amount related to concentration in the body fluid sample, (ii) generates an assay result indicative of binding of C-C motif chemokine 4 to the binding reagent; and (iii) displays the assay result as a quantitative result in a human-readable form;
    diagnosing the subject with appendicitis based on the assay result; and
    treating the subject diagnosed with appendicitis by appendectomy.

12. The method according to claim 11, wherein the assay result is displayed as a concentration of C-C motif chemokine 4.

13. The method according to claim 11, wherein the analyte binding assay is an immunoassay, wherein step (i) comprises contacting the body fluid sample with the binding reagent on an assay device, wherein the binding reagent is a plurality of antibodies specific for C-C motif chemokine 4, and wherein the generated assay result of (ii) is indicative of binding of C-C motif chemokine 4 to the plurality of antibodies.

14. The method of claim 11, wherein the body fluid sample is selected from the group consisting of urine, blood, serum, and plasma.

15. The method of claim 14, wherein the body fluid sample is urine or plasma.

\* \* \* \* \*